United States Patent
Op Den Buijs et al.

(10) Patent No.: US 11,806,130 B2
(45) Date of Patent: Nov. 7, 2023

(54) PREDICTING THE PROBABILITY OF A BRAIN INJURY OF A SUBJECT RESULTING FROM A FALL

(71) Applicant: KONINKLIJKE PHILIPS N.V., Eindhoven (NL)

(72) Inventors: Jorn Op Den Buijs, Eindhoven (NL); Marten Jeroen Pijl, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 295 days.

(21) Appl. No.: 17/120,366

(22) Filed: Dec. 14, 2020

(65) Prior Publication Data
US 2021/0369142 A1 Dec. 2, 2021

(30) Foreign Application Priority Data
Dec. 18, 2019 (EP) .................................. 19217567

(51) Int. Cl.
 *A61B 5/11* (2006.01)
 *G16H 50/30* (2018.01)
 *G16H 50/20* (2018.01)
 *A61B 5/00* (2006.01)

(52) U.S. Cl.
 CPC .......... *A61B 5/1117* (2013.01); *A61B 5/4064* (2013.01); *G16H 50/20* (2018.01); *G16H 50/30* (2018.01)

(58) Field of Classification Search
CPC .... A61B 5/1117; A61B 5/4064; G16H 50/20; G16H 50/30; G16H 40/63
See application file for complete search history.

(56) References Cited

U.S. PATENT DOCUMENTS

| | | | |
|---|---|---|---|
| 9,107,615 B2* | 8/2015 | Buckman | G01C 19/04 |
| 9,936,756 B1 | 4/2018 | Yu et al. | |
| 2006/0001545 A1* | 1/2006 | Wolf | G08B 21/0446 340/686.1 |
| 2016/0106346 A1* | 4/2016 | Benzel | A61B 5/1122 600/595 |
| 2016/0256346 A1* | 9/2016 | Stockmaster | G16H 40/63 |
| 2018/0233018 A1* | 8/2018 | Burwinkel | A61B 5/1117 |

(Continued)

FOREIGN PATENT DOCUMENTS

WO 2012009331 A2 1/2012

OTHER PUBLICATIONS

Michael W. Dusenberry, Charles K. Brown, Kori L. Brewer, Artificial neural networks: Predicting head CT findings in elderly patients presenting with minor head injury after a fall, The American Journal of Emergency Medicine, vol. 35, Issue 2, 2017, pp. 260-267.

(Continued)

*Primary Examiner* — Eric F Winakur
*Assistant Examiner* — Jonathan Drew Moroneso (57) ABSTRACT

Proposed are concepts for predicting the likelihood of a brain injury of a subject resulting from a fall event experienced by the subject. Such concepts may therefore be useful for determining a need for further medical assessment or treatment of a fall by the subject. According to an exemplary concept, data from one or more sensors is used to determine information about a fall of a subject. Such information is then used in conjunction with a prediction algorithm to derive a probability of a brain injury.

20 Claims, 5 Drawing Sheets

(56) References Cited

U.S. PATENT DOCUMENTS

2018/0360349 A9 12/2018 Dohrmann et al.
2019/0122532 A1 4/2019 Pauws et al.
2019/0307328 A1 10/2019 Tran

OTHER PUBLICATIONS

Molaei, S., "A machine learning based approach for identifying traumatic brain injury patients for whom a head CT scan can be avoided", IEEE, 2016.

* cited by examiner

PREDICTING THE PROBABILITY OF A BRAIN INJURY OF A SUBJECT RESULTING FROM A FALL

CROSS-REFERENCE TO PRIOR APPLICATIONS

This application claims the benefit of European Patent Application No. 19217567.7, filed on 18 Dec. 2019. This application is hereby incorporated by reference herein.

FIELD OF THE INVENTION

The invention relates to the field of clinical support, and more particularly to predicting the probability of a brain injury of a subject resulting from a fall.

BACKGROUND OF THE INVENTION

Current clinical guidelines recommend that certain types or classes of individuals (such as those aged 65 and over) should receive certain medical assessment and treatment (e.g. a head CT scan) after a fall resulting in an impact to the head (e.g. a fall that may have caused a brain injury). However, such assessments and/or treatments may be costly and carry associated drawbacks or side-effects (e.g. increased radiation risk). To contain costs while providing appropriate care or medical treatment, it is important to know when a subject will benefit from a particular medical assessment and/or treatment.

A conventional approach to identifying when a subject will benefit from a particular medical assessment and/or treatment is to have a medical professional ask questions to the subject (i.e. interview the subject). This is done in manner which attempts to obtain information that may be useful for estimating the likelihood of a brain injury and/or the need for further medical assessment and/or/treatment. However, asking numerous and/or potentially difficult questions to a subject after a fall has occurred may not obtain accurate information for indicating a potential need for further medical assessment and/or treatment. Such an interview process may also delay the provision of further of vital medical assessment and/or treatment.

SUMMARY OF THE INVENTION

The invention is defined by the claims.

According to examples in accordance with an aspect of the invention, there is provided a computer-implemented method for predicting the probability of a brain injury of a subject resulting from a fall by the subject. The method comprises: obtaining fall data representative of a movement or a force of the fall; obtaining subject data representative of at least one property of the subject; providing the fall data and the subject data to a prediction algorithm; and obtaining a prediction result from the prediction algorithm based on the fall data and the subject data, the prediction result representing a probability of a brain injury of the subject resulting from the fall by the subject.

Proposed are concepts for predicting the likelihood of a brain injury of a subject resulting from a fall event experienced by the subject. Such concepts may therefore be useful for determining a need for further medical assessment or treatment of a fall by the subject. For instance, a need for a head CT scan after a fall may be determined. Embodiments may therefore automatically and dynamically identify requirements for medical attention. In this way, the unnecessary use of medical resources may be avoided whilst ensuring appropriate medical attention/care is provided, thus optimizing use of medical resources (e.g. in terms of cost, availability and usage).

Proposals are directed towards providing (potentially valuable) information about the probability of a brain/head injury from a fall of a subject. Such information may, for example, be crucial for determining a need for medical intervention/treatment (as may be done by a medical professional). The inventors have identified that subject monitoring systems and Personal Emergency Response Systems (PERS) typically monitor subjects with one or more sensors and thus collect data that may be leveraged to determine information about a fall of a subject. Such information may then be used in conjunction with a prediction algorithm to derive a probability of a brain injury. For instance, some existing PERS devices contain sensors (e.g. a pressure sensor, accelerometers, etc.) that are adapted to sense movement of the subject and/or force experienced by a monitored subject (e.g. patient) for automated fall detection. It is proposed that data/information from such sensors may be to derive descriptive parameters of a fall, which may in turn be informative regarding the potential of a brain injury resulting from the fall.

In contrast to conventional questioning/interview approaches, a monitoring system or PERS may be used to collect information about the subject (i.e. subject data representative of at least one property of the subject, such as age; existing injury; medical condition; weight; gender; prescribed medication, etc.). Further, case data and first-aider/responder notes (e.g. presence of a fall with head injury and type of fall) about a fall event may also be obtained. Various forms of information and data may thus be collated and input to a prediction algorithm to determine a prediction result representing a probability of a brain injury of the subject resulting from the fall. By including fall data representative of movement or force of the actual fall (i.e. sensor data obtained for the fall) within the determination, a more accurate understanding of the fall may be obtained. This may be because sensor-based data is more reliable than subject-reported data.

By way of example, in some proposed embodiments, a PERS may be used to collect: fall data representative of a movement or a force of a fall; and subject data representative of at least one property of the subject. This information may then be input into a prediction model to automatically generate a report for a medical professional, wherein the report includes an indication of the probability/likelihood of a brain injury of the subject resulting from the fall and/or the need for a head CT scan. Such embodiments may therefore leverage sensor measurements (e.g. accelerometer and pressure sensor measurement) taken during the fall so as to improve accuracy of the prediction result from the prediction model.

In particular, embodiments may be used in relation to a subject (e.g. a patient) so as optimize implementation or allocation of the medical assessment, therapy and/or treatment for the subject. Such embodiments may support clinical planning. Improved Clinical Decision Support (CDS) may therefore be provided by proposed concepts.

Also, the collection and analysis of data relating to movement and/or force of a subject's fall facilitate tailored diagnostics. Proposed approaches may focus on the combination of data relating to a subject and data relating to a fall of the subject to enable efficient and accurate brain injury prediction. By way of example, this may provide for: reduced subject administration or interrogation; improved injury management; and iterative improvement of subject/ fall-specific diagnostics, treatment and management.

In some embodiments, providing the fall data to the prediction algorithm may comprise: processing the fall data to determine a value of a parameter of the fall; and inputting the determined value of the parameter of the fall to the prediction algorithm. By way of example, the parameter of the fall may comprise: duration of the fall; height of the fall; impact type; and speed of fall. Various properties or characteristics of the fall may therefore be determined from the fall data, and then this may be used for obtaining a prediction result. Such properties/characteristics of fall may directly (or indirectly) influence a probability of a brain injury of the subject resulting from a fall, and so proposed embodiments may account for this through use of such properties/characteristics in a prediction algorithm. Proposed embodiments may therefore leverage a realisation that fall data representative of a movement or a force of a fall may be used to determine one or more properties/characteristics of the fall that may influence or affect a probability of a brain injury resulting from the fall. By determining such properties/ characteristics from the fall data and then accounting for such a dependency, embodiments may provide more accurate prediction results.

Some embodiments may be configured to determine the fall data. For example, in such embodiments, obtaining fall data may comprise: monitoring the subject with at least one of a movement sensor and a force sensor to generate at least one of: movement data representative of movement of the subject; and force data representative of force experienced by the subject; detecting a fall by the subject; and, responsive to detecting a fall by the subject, determining a time of the fall and generating fall data comprising the generated movement data and/or force data for a time period including the time of the fall. Thus, rather than relying on information about the subject from a separate monitoring system, embodiments may be configured to monitoring the subject in order to detect potential fall event and determine fall data representative of a movement or a force of the fall. For instance, an embodiment may comprise a subject monitoring system or a PERS system with improved or extended functionality provided as a result of the proposed concept(s). Purely by way of further example, an embodiment may comprise a PERS system that is adapted to predict a probability of a brain injury of the subject resulting from a fall by the subject, and such a prediction may use fall data and the subject data in a prediction algorithm.

Conversely, in other embodiments, fall data may be obtained from a separate and/or remotely-located information source (e.g. a fall detection system, subject monitoring system, PERS device, etc.). In this way, embodiments may be configured to simply receive information about a subject and a fall of subject, and then employ the received information in a prediction algorithm to determine a probability of a brain injury of the subject resulting from the fall.

For instance, in some embodiments, obtaining fall data may comprise receiving, from at least one of a movement sensor and a force sensor: movement data representative of movement of the subject; and force data representative of force experienced by the subject for a time period including the time of the fall. Proposed embodiments may therefore leverage information from existing fall monitoring or detection systems in order to dynamically and flexibly determine a probability of a brain injury of a subject resulting from a fall. Embodiments may thus increase a value of existing/ conventional fall detection systems by providing modified and/or extended functionality.

By way of example, the at least one property of the subject may comprise at least one of: age; existing injury; medical condition; weight; gender; prescribed medication; ethnicity; housebound status; living alone; use of cane/crutches/ walker/wheelchair; previous falls; acute illness; cognitive impairment; reduced vision (i.e., decline in visual acuity; decline in accommodative capacity; glare intolerance; altered depth perception; presbyopia [near vision]; decreased night vision; decline in peripheral vision); difficulty rising from a chair; loss of coordination; reflexes/ slowed reaction time; presence of osteoporosis or other bone degenerative diseases; foot problems; presence of environmental hazards in the home; risky behaviours (e.g. sports, hobbies, etc.). Various properties or characteristics of the monitored subjects may therefore be used for obtaining a prediction result, and the properties/characteristics may be physiological (and fixed or slow changing) and/or situational (and thus variable with respect to time). Such properties/ characteristics may directly (or indirectly) influence a probability of a brain injury of the subject resulting from a fall, and so proposed embodiments may account for this through use of such properties/characteristics in a prediction algorithm. Proposed embodiments may therefore leverage a realisation that a property of a monitored subject may influence or affect a probability of a brain injury resulting from the fall. By accounting for such a dependency, embodiments may provide more accurate prediction results.

Some embodiments may further comprise obtaining event data representative of at least one descriptor of the fall; providing the event data to the prediction algorithm; and obtaining a prediction result from the prediction algorithm further based on the event data. By way of example the at least one descriptor of the fall may comprise: location; fall type; resultant injury; received treatment; resultant symptom (s). Various descriptive properties or characteristics of the fall may therefore be used for obtaining a prediction result. Such properties/characteristics may provide useful indications about a probability of a brain injury of the subject resulting from a fall, and so proposed embodiments may account for this through use of such properties/characteristics in a prediction algorithm. Proposed embodiments may therefore leverage a realisation that a various aspects of the fall, its situation and/or its context may provide useful information that can be leveraged for the purpose of estimating the probability of a brain injury resulting from the fall. By leveraging such information, embodiments may provide more accurate prediction results.

The prediction algorithm may comprise a machine-learning algorithm that is trained using a training algorithm configured to receive an array of training inputs and known outputs. By way of example, a training input may comprise at least one of: a property; movement; and force of a subject that experienced a fall, and wherein a known output for a training input may comprise a probability of a brain injury. In this way, the prediction algorithm may be trained to output an accurate prediction result representing a probability of a brain injury of the subject resulting from the fall by the subject.

In some embodiments, the prediction algorithm may comprise at least one of: a rule-based algorithm; an artificial neural network-based learning algorithm; a decision tree-based algorithm; and a logic regression algorithm. Various types of conventional prediction algorithms may therefore be employed by proposed embodiments, thus reducing complexity and/or cost of implementation.

There may also be proposed a computer-implemented method for estimating a need for a head CT scan of a subject.

Such a method may comprise: predicting the probability of a brain injury of the subject resulting from a fall by the subject according to a proposed embodiment; and estimating the need for a head CT scan of the subject based on the predicted probability of a brain injury of the subject.

According to examples in accordance with an aspect of the invention, there is provided a computer program comprising code means for implementing the method of any previously described method when said program is run on a processing system.

According to another aspect of the invention, there is provided a system for predicting a probability of a brain injury of a subject resulting from a fall by the subject. The system comprises: an input interface configured to obtain fall data representative of a movement or a force of the fall, and to obtain subject data representative of at least one property of the subject; and a prediction unit configured to generate a prediction result by processing the fall data and the subject data with a prediction algorithm, the prediction result representing a probability of a brain injury of the subject resulting from the fall by the subject.

There is also proposed a system for estimating a need for a head CT scan of a subject. The system comprises a system for predicting a probability of a brain injury of a subject resulting from a fall by the subject according to a proposed embodiment; and a an estimation component configured to estimate the need for a head CT scan of the subject based on the predicted probability of a brain injury of the subject.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

It should be understood that the Figures are merely schematic and are not drawn to scale. It should also be understood that the same reference numerals are used throughout the Figures to indicate the same or similar parts.

Proposed are concepts for predicting the probability of a brain injury of a subject resulting from a fall by the subject. Such concepts may therefore be used for identifying a need for further medical assessment or treatment of a fall by the subject.

In particular, proposed concepts realize that subject monitoring systems and Personal Emergency Response Systems (PERS) typically monitor subjects with one or sensors and thus collect data that may be leveraged to determine information about a fall of a subject.

By way of example, existing fall detection systems typically consist of two phases. In a first phase, values for parameters that may indicate the likelihood of a fall are obtained for an event from data from sensors such as accelerometers and barometric sensors. Other sensors may include gyroscopes, magnetometers, ultrasound sensors, radar sensors, skin conductivity sensors and pulse (PPG) sensors, for example. The parameters may include any of height, height change, orientation, orientation change, velocity, duration and impact (distance, physiological quantities). Events are typically defined using a trigger, which monitors at least one trigger parameter: an event is considered to have occurred at the point at which the value of a trigger parameter exceeds or falls below a corresponding predetermined trigger threshold value (or when a change of a value is greater than a predetermined change). For example, an event may be detected when the barometer indicates a height drop of more than 50 cm, or the accelerometer indicates an acceleration of more than 2 g.

In a second phase, a classifier (e.g. a processing device) takes one or more of the obtained parameter values from the event and outputs a value indicating or predicting whether or not the event is a fall. In some cases, the obtained parameter value(s) are used to calculate a probability that a fall has occurred, e.g. using a fall event probability distribution, and the classifier applies a threshold to the calculated probability to decide whether that probability is predict, with a certain degree of accuracy, whether or not a fall has occurred.

According to a concept of the invention, it is proposed that data from one or more sensors may be used to determine information about a fall of a subject. Such information may then be used in conjunction with a prediction algorithm to derive a probability of a brain injury. For instance, an artificial neural network (ANN) has already been developed to determine the probability of needing a head CT scan after a fall on the head, and the input parameters for the ANN include age, gender, type of fall, presence of dementia, use of anti-coagulants, and presence of injuries above the clavicle. The model employed by the known ANN was trained to identify cases with positive findings on a head CT scan. Proposed embodiments may thus employ and build upon such a known ANN to make use of fall data obtained from one or more sensors. In this way, a property/characteristic specific to a fall of a subject (which may influence a probability of resulting head injury) may be accounted for, thereby providing for tailored and accurate brain/head injury prediction.

Illustrative embodiments may, for example, be employed in (or in conjunction with) fall detectors and/or fall detection systems. Such detectors and/or systems may be used in PERS systems at a subject's home or in specialized accommodation such as Senior Living Facilities, in hospital products, and/or using apps designed for smartwatches.

Embodiments of the present invention are therefore directed toward enabling fall-specific and/or subject-specific assessment so as to facilitate or enhance a CDS process. Further, embodiments may be aimed at enabling the provision of fall/subject-specific therapy or treatment that make use of resources in an optimal manner. By way of example only, illustrative embodiments may be utilized in many different types of clinical, medical or subject-related environments, such as a hospital, doctor's office, ward, care home, person's home, etc.

As mentioned above, proposed concepts are at least partly based on the realization that a sensed fall data may be used in conjunction with data about the subject that fell.

Figure 1:
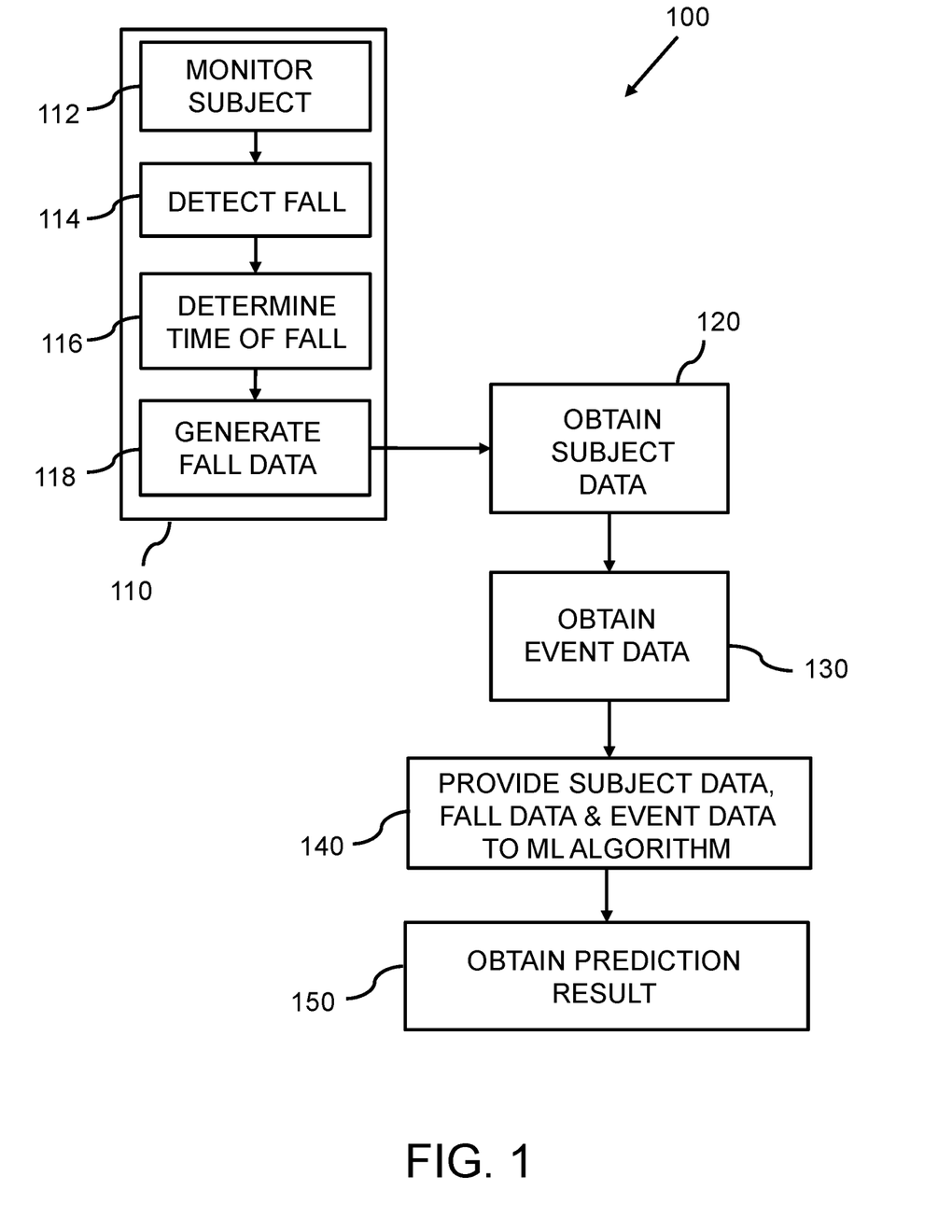
FIG. 1 is a flow diagram of a method for predicting the probability of a brain injury of a subject resulting from a fall by the subject according to a proposed embodiment.

FIG. 1 illustrates a method 100 for predicting the probability of a brain injury of a subject resulting from a fall by the subject according to a proposed embodiment. Such a method may be used, for example, for estimating a need for a head CT scan of the subject as a result of the fall.

The method begins with step 110 of obtaining fall data representative of a movement or a force of the fall. Here, the method is configured to determine the fall data (rather than simply obtain it from a separate system for example). In particular, step 110 comprises sub-steps 112-118. Step 112 comprises monitoring the subject with at least one of a movement sensor and a force sensor to generate at least one of: movement data representative of movement of the subject; and force data representative of force experienced by the subject. Step 114 then comprises detecting a fall by the subject. Responsive to detecting a fall by the subject, the method proceeds to step 116 of determining a time of the fall and, subsequently, fall data comprising the generated movement data and/or force data for a time period including the time of the fall is generated in step 118.

Thus, rather than relying on information about the fall from a separate monitoring system, the embodiment of FIG. 1 is configured to monitor the subject in order to detect a fall event and determine fall data representative of a movement or a force of the fall.

Next, in step 120, subject data representative of at least one property of the subject is obtained (e.g. from a remote database adapted to store data about one or more monitored subjects). By way of example, a property of the subject may comprise: age; existing injury; medical condition; weight; gender; or prescribed medication; ethnicity; housebound status; living alone; use of cane/crutches/walker/wheelchair; previous falls; acute illness; cognitive impairment; reduced vision (i.e., decline in visual acuity; decline in accommodative capacity; glare intolerance; altered depth perception; presbyopia [near vision]; decreased night vision; decline in peripheral vision); difficulty rising from a chair; loss of coordination; reflexes/slowed reaction time; presence of osteoporosis or other bone degenerative diseases; foot problems; presence of environmental hazards in the home; risky behaviours (e.g. sports, hobbies, etc.). Such properties/ characteristics may directly (or indirectly) influence a probability of a brain injury of the subject resulting from a fall, and so, by obtaining subject data representative of at least one property of the subject, account may be taken of such influence(s).

The method then proceeds to step 130 of obtaining event data representative of at least one descriptor of the fall. Purely by way of example, a descriptor of the fall may comprise: location; fall type; resultant injury; or received treatment. Event data may thus provide further information the situation of the fall and/or its context, and this may, in turn, provide useful information that can be leveraged for the purpose of more accurately estimating the probability of a brain injury resulting from the fall.

The obtained fall data, event data and subject data is provided to a prediction algorithm in step 140. Here, the fall data is firstly analyzed so as to determine a value of a parameter of the fall, such as duration of the fall; height of the fall; impact type; or speed of fall for example. The determined value of at least parameter of the fall is then input to the prediction algorithm.

By way of example, the prediction algorithm of this example employs an artificial neural network-based learning algorithm. An ANN has already been developed by Dusenberry M W, Brown C K, Brewer K L to determine the probability of needing a head CT scan after a fall on the head (Artificial neural networks: Predicting head CT findings in elderly patients presenting with minor head injury after a fall. (Am J Emerg Med. 2017; 35: 260-267. doi:10.1016/j.ajem.2016.10.065). This known ANN may be adapted and employed by this embodiment. However, other embodiments may alternatively, or additionally employ a decision tree-based algorithm and/or a logic regression algorithm. The prediction algorithm is trained using a training algorithm configured to receive an array of training inputs and known outputs. In this example, the training input comprises at least one of: a property; movement; and force of a subject that experienced a fall. Also, a known output for a training input comprises a probability of a brain injury.

Finally, step 150 comprises obtaining a prediction result from the prediction algorithm based on the fall data, event data and the subject data. The prediction result includes a prediction/estimate of a probability of a brain injury of the subject resulting from the fall by the subject (as derived by the prediction algorithm).

Although, in the above-described embodiment of FIG. 1, the step 110 of obtaining fall data is undertaken by monitoring the subject to detect a fall and then determining fall data for a detected fall, it will be appreciated that, in other embodiments, the fall may simply be obtained from a separate and/or remotely-located information source (e.g. a fall detection system, database of fall cases, subject monitoring system, etc.). In this way, such alternative embodiments may be configured to simply receive fall data representative of a movement or a force of a fall, and then employ the received fall data (in combination with subject data) to determine a probability of a brain injury of the subject resulting from the fall.

By way of further illustration of the proposed concept(s), a system for predicting a probability of a brain injury of a subject resulting from a fall according to an embodiment will be now be described with reference to FIG. 2.

Figure 2:
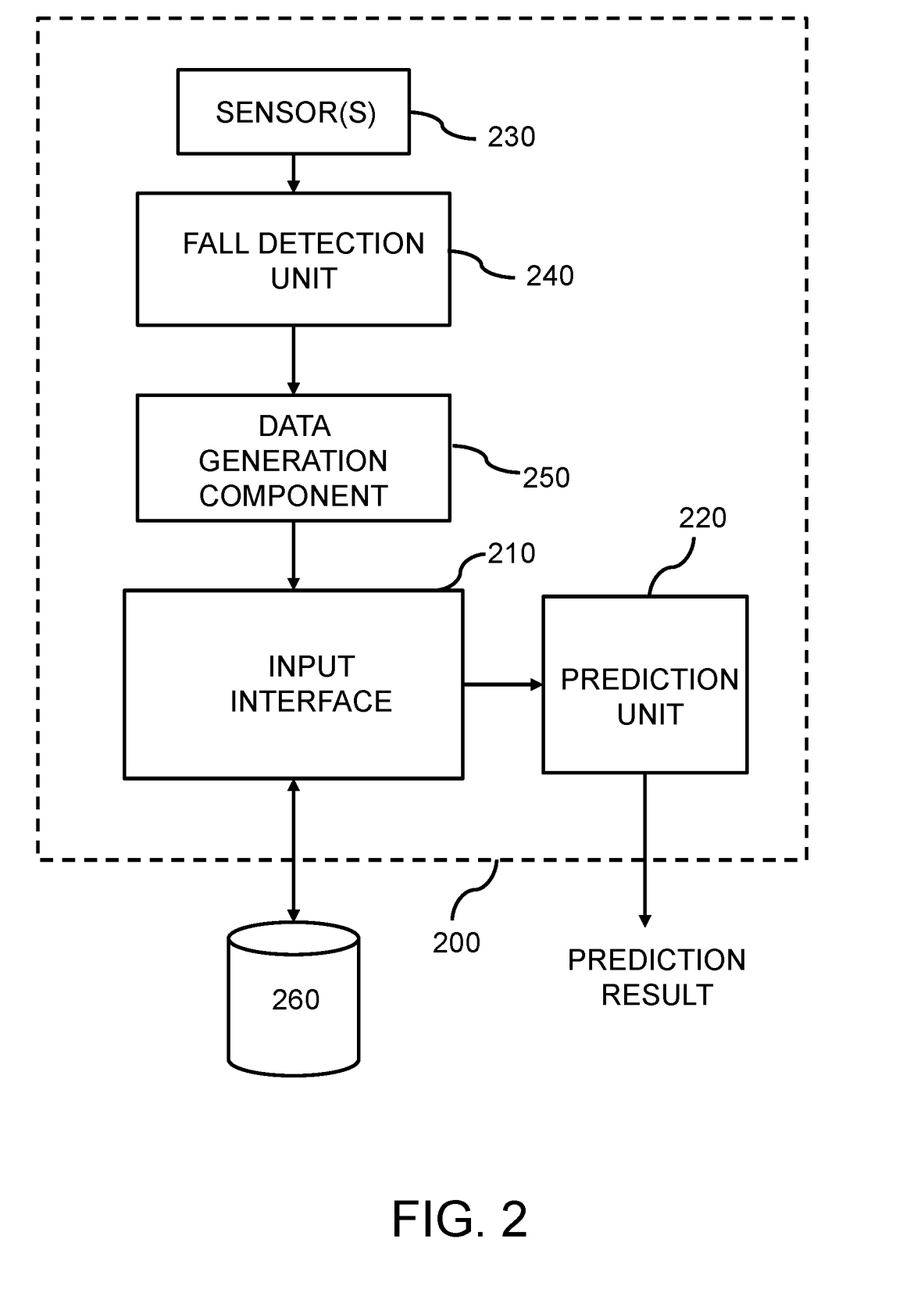
FIG. 2 illustrates a system for predicting a probability of a brain injury of a subject resulting from a fall according to an embodiment.

FIG. 2 illustrates a system 200 for predicting a probability of a brain injury of a subject resulting from a fall according to an embodiment. The system comprises an input interface 210 configured to obtain fall data representative of a movement or a force of the fall, and to obtain subject data representative of at least one property of the subject. The system 200 also comprises a prediction unit 220 configured to generate a prediction result by processing the fall data and the subject data with a prediction algorithm. The prediction result is provided as an output from the prediction unit 220 and represents a probability of a brain injury of the subject resulting from the fall by the subject.

In the system 200 of FIG. 2, the fall data is generated within the system and provided to the input interface 210. More specifically, the system 200 comprises a movement sensor 230 and/or a force sensor 230 configured to, respectively, generate movement data representative of movement of the subject and/or force data representative of force experienced by the subject. The system 200 also comprises a fall detection unit 240 that is configured to detect a fall by the subject based on the movement data and/or force data from the sensors 230. Such fall detection based on sensed data employs conventional and widely-adopted fall detection algorithms, and so detailed description of such algorithms is hereby omitted. A data generation component 250 of the system is then configured, responsive to detecting a fall by the subject, to determine a time of the fall and to generate fall data comprising the generated movement data and/or force data for a time period including the time of the fall. In this way, the input interface 210 is arranged to obtain fall data representative of a movement or a force of the fall.

Further, the subject data representative of at least one property of the subject is arranged to be retrieved from a remotely located database of subjects (e.g. subscribers of the system) via an appropriate communication link. For example, the database may store various types of information about each of a plurality of subjects. Such information may, for example, be provided to the based during an enrolment process which requires a subject (e.g. subscriber of the system) to provided various details (such as age; existing injury; medical condition; weight; gender; prescribed medication) when registering to use the system.

As mentioned above, a prediction result provided by a proposed embodiment (such as that depicted in FIG. 2) may be useful to the purpose of estimating a need for a head CT scan of a subject following a fall. A system may therefore be provided which includes a proposed embodiment of a system for predicting a probability of a brain injury of a subject resulting from a fall.

Figure 3:
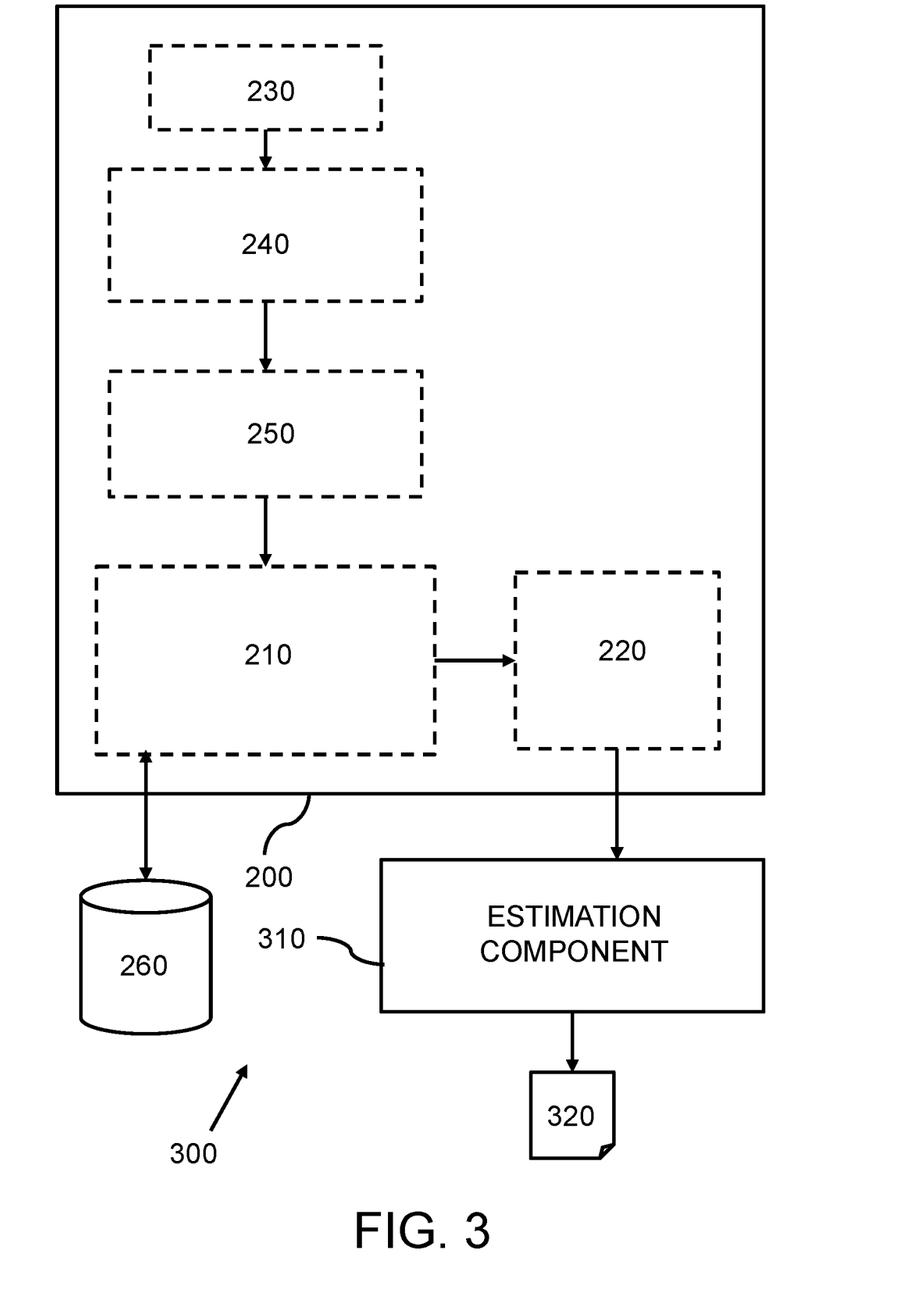
FIG. 3 illustrates a system for estimating a need for a head CT scan of a subject according to an embodiment.

By way of example, FIG. 3 illustrates a system 300 for estimating a need for a head CT scan of a subject according to an embodiment of the invention. The system 300 comprises the system 200 of FIG. 2 (for predicting a probability of a brain injury of a subject resulting from a fall) and an estimation component 310. The estimation component 310 is configured to estimate the need for a head CT scan of the subject based on a predicted probability of a brain injury of the subject provided to it from the system 200 of FIG. 2. The output of the estimation component 310 in this example is a report 320 which includes the estimate determined by the estimation component 310.

Figure 4:
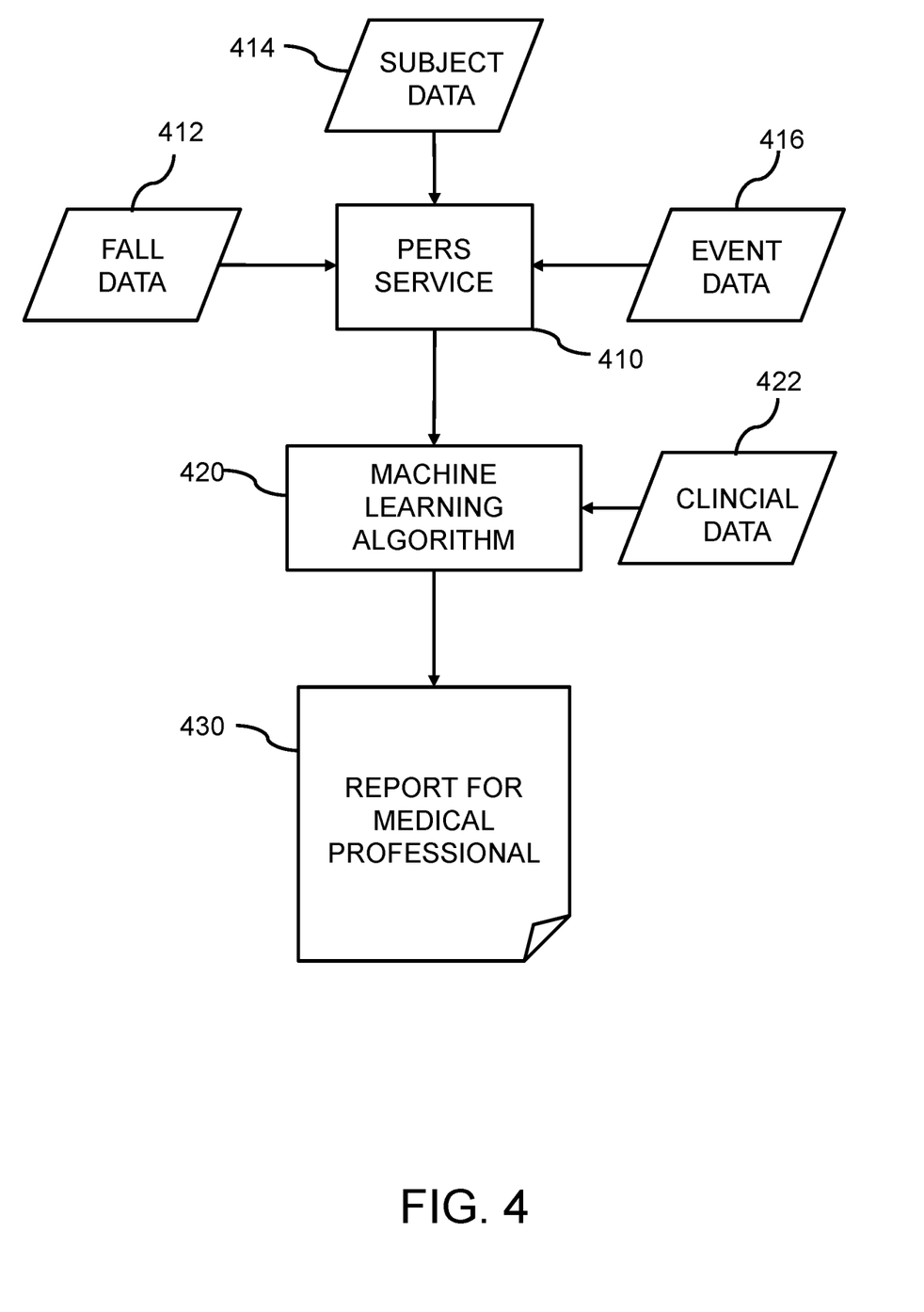
FIG. 4 is a simplified block diagram of an exemplary embodiment.

Referring now to FIG. 4, there is depicted a simplified block diagram of an exemplary embodiment. The main elements of the embodiment are as follows 410—A PERS service configured to collect data for a prediction model, namely: fall data 412 from one or more sensors (such accelerometers and/or a pressure sensor); subject data 414 from an enrolment database (storing information such as demographics, medication conditions, medication usage, etc.); and event data 416 from a case report (comprising information such as fall event situation, event outcome (e.g. hospitalization), and event notes (e.g. type of fall, type of injury, etc.)).

420—A machine learning module (i.e. prediction unit) that is configured to use the input data collected by the PERS service 410 to calculate a probability of needing a head CT scan. The machine learning model is trained using historical clinical data 422 using methods such as logistic regression, neural networks, support vector machines, or decision trees.

The machine learning module 420 generates and sends a report 430 to user (e.g. medical professional, carer or emergency physician). An addition to the calculated probability of needing a head CT scan, the report 430 including information about the subject, and characteristics of the fall (as collected by the PERS service for example).

Figure 5:
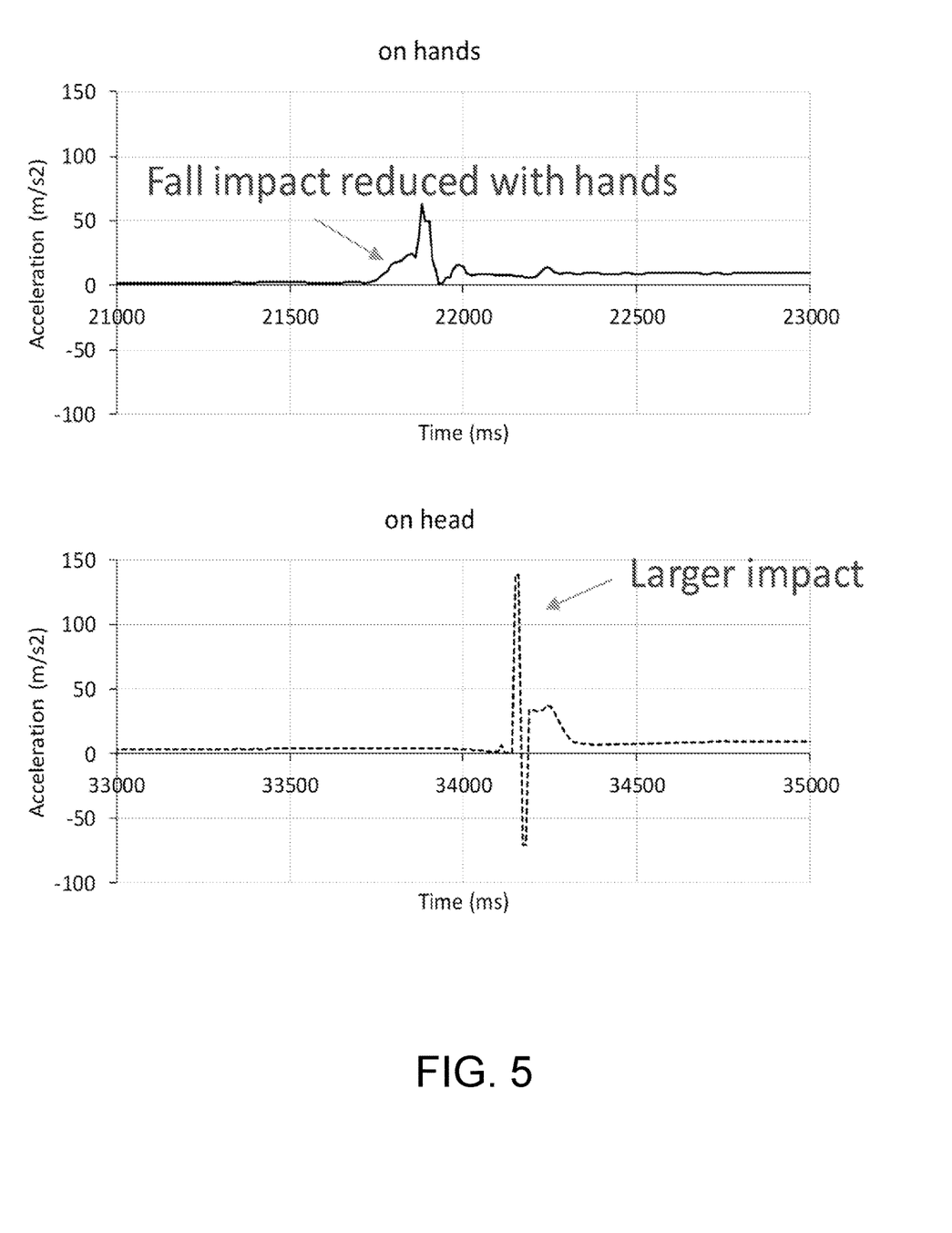
FIG. 5 shows exemplary accelerometer data of (imitated) falls, wherein the accelerometer was in a smartphone carried/worn on the chest area of a subject; the top plot of data shows accelerometer data for a fall event wherein the subject fell mainly on his/her hands, and the bottom plot of data shows accelerometer data wherein the subject fell was directly on his her/head (onto a pillow).

Simply by way of further explanation, FIG. 5 shows exemplary accelerometer data of (imitated) falls, wherein the accelerometer was in a smartphone carried/worn on the chest area of a subject. The top plot of data shows accelerometer data for a fall event wherein the subject fell mainly on his/her hands. The bottom plot of data shows accelerometer data wherein the subject fell was directly on his her/head (onto a pillow). Parameters of the fall that are derived from the fall data (i.e. sensor data) are: the duration of the fall; the height of peak acceleration; the area under the curve during the fall; and presence of a smaller bump before the main peak to indicate the pattern of the fall (e.g., breaking the fall with the hands).

Thus, it will be appreciated that fall data obtained from one or more sensors can be processed to determine a value of each of one or more parameters of a fall.

By way of yet further example, one may consider a situation where a subject is a subscriber of a PERS service and has a pendant or wrist device with sensors for automated fall detection. When the subject has an incident (such as a fall), he/she connects (via the PERS device or a separate communicator) to a response resource of the PERS service, where a response agent assesses the situation and sends the appropriate type of help to the subject's home. The response agent logs characteristics of the incident in a structured and/or unstructured electronic case record. This may include whether or not the incident was a fall, what was the type of fall (from sitting, standing, bed or height) and what was the type of injury (e.g. head injury). The response agent also records the type of help (outcome) of the case, e.g. transport by ambulance to the hospital.

Furthermore, during PERS service enrolment, subscriber information (i.e. information about the subject) is logged (such as age, gender, medication, etc.).

When a subject calls for help and the incident is logged as a fall (either through subscriber reporting or via the automated fall detection), and further the incident results in a transport to the hospital, subject data, fall data and event data is retrieved from the PERS enrolment database, case database and the sensor(s). The prediction model then uses this data to predict the likelihood of needing a head CT scan. Finally, a report including the determined probability is then generated and sent to an appropriate medical professional, medical facility and/or carer. The report can also include the patient information, the values of the predictors leading to the predicted probability, and a time trace of the fall. Alternatively, or additionally, the probability can be transferred electronically into health records for the subject.

It will be understood that the disclosed methods are computer-implemented methods. As such, there is also proposed a concept of a computer program comprising code means for implementing any described method when said program is run on a processing system.

The skilled person would be readily capable of developing a processor for carrying out any herein described method. Thus, each step of a flow chart may represent a different action performed by a processor, and may be performed by a respective module of the processing processor.

As discussed above, the system makes use of a processor to perform the data processing. The processor can be implemented in numerous ways, with software and/or hardware, to perform the various functions required. The processor typically employs one or more microprocessors that may be programmed using software (e.g. microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted that the term "adapted to" is intended to be equivalent to the term "configured to". Any reference signs in the claims should not be construed as limiting the scope.

The invention claimed is:

1. A method for predicting a probability of a brain injury of a subject resulting from a fall by the subject, the method comprising:
    obtaining fall data representative of a movement or a force of the fall;
    obtaining subject data representative of at least one property of the subject;
    obtaining event data representative of at least one descriptor of the fall indicating at least one of a situation or context of the fall;
    providing the fall data, the subject data and the event data to a computer-implemented prediction algorithm;
    obtaining a prediction result from the prediction algorithm based on the fall data, the subject data, and the event data, the prediction result indicating a probability of a brain injury of the subject resulting from the fall by the subject, and
    determining a need for further medical assessment or medical treatment of the subject based on the predicted probability of the brain injury.

2. The method of claim 1, wherein providing the fall data to the prediction algorithm comprises:
    processing the fall data to determine a value of a parameter of the fall; and
    inputting the determined value of the parameter of the fall to the prediction algorithm.

3. The method of claim 2, wherein the parameter of the fall comprises: duration of the fall; height of the fall; impact type; and speed of fall.

4. The method of claim 1, wherein obtaining the fall data comprises:
    monitoring the subject with at least one of a movement sensor to generate movement data representative of movement of the subject and a force sensor to generate force data representative of force experienced by the subject;
    detecting a fall by the subject; and
    responsive to detecting the fall by the subject, determining a time of the fall and generating the fall data comprising the generated movement data and/or force data for a time period including the time of the fall.

5. The method of claim 1, wherein obtaining the fall data comprises:
    receiving, from at least one of a movement sensor and a force sensor: movement data representative of movement of the subject, and force data representative of force experienced by the subject for a time period including the time of the fall.

6. The method of claim 1, wherein the at least one property of the subject comprises at least one of:
    age; existing injury; medical condition; weight; gender; prescribed medication; ethnicity; housebound status; use of cane/crutches/walker/wheelchair; acute illness; cognitive impairment; vision; accommodative capacity; glare intolerance; depth perception; presbyopia; night vision; peripheral vision; coordination; reflexes; and risky behaviours.

7. The method of claim 1, wherein the at least one descriptor of the fall comprises at least one of:
    a location of the fall; a fall type; a resultant injury; or a received treatment.

8. The method of claim 1, further comprising:
    training the prediction algorithm using a training algorithm configured to receive an array of training inputs and known outputs, wherein a training input comprises at least one of: a property; movement; and force of a subject that experienced a fall, and wherein a known output for a training input comprises a probability of a brain injury.

9. The method of claim 1, wherein the prediction algorithm comprises at least one of: a rule-based algorithm; an artificial neural network-based learning algorithm; a decision tree-based algorithm; or a logic regression algorithm.

10. The method of claim 1,
    wherein determining the need for further medical assessment or medical treatment of the subject comprising estimating a need for a head assessment or medium treatment of the subject comprises estimating a need for a head CT scan of the subject based on the predicted probability of the brain injury of the subject.

11. The method of claim 1, wherein each of the fall data, the subject data, and the event data is received from a Personal Emergency Response Systems (PERS) previously configured to monitor the subject.

12. A non-transitory computer readable medium storing instructions, for predicting a probability of a brain injury of a subject resulting from a fall by the subject, that when executed by a processor, cause the processor to:
- receive fall data from at least one sensor worn but the subject,
- receiving subject data representative of at least one property of the subject;
- receive event data representative of at least one descriptor of the fall indicating at least one of a situation or context of the fall;
- generate a prediction result by processing the fall data, the subject data, and the event data with a prediction algorithm, the prediction result indicating a probability of a brain injury of the subject resulting from the fall by the subject, and
- estimate a need of fall specific and subject therapy of treatment of the subject based on the probability of the brain injury.

13. The computer readable medium of claim 12, wherein the instructions further cause the processor to process the fall data to determine a value of a parameter of the fall; and to input the determined value of the parameter of the fall to the prediction algorithm as the fall data.

14. The computer readable medium of claim 13, wherein the parameter of the fall comprises at least one of duration of the fall, height of the fall, impact type, or speed of fall.

15. The computer readable medium of claim 12, wherein the instructions further cause the processor to retrieve each of the fall data, the subject data, and the event data is received from a Personal Emergency Response Systems (PERS) previously configured to monitor the subject.

16. A system for predicting a probability of a brain injury of a subject resulting from a fall by the subject, the system comprising:
- at least one sensor configured to generate at least one of movement data representative of movement of the subject and force data representative of force experienced by the subject, respectively;
- a processor in communication with the at least one sensor; and
- a non-transitory storage medium storing instructions that, when executed by the processor, cause the processor;
- receive fall data from the at least one sensor;
- receive subject data representative of at least one property of the subject;
- receive event data representative of at least one descriptor of the fall indicating at least one of a situation or context of the fall; and
- generate a prediction result by processing the fall data, the subject data, and the event data with a prediction algorithm, the prediction result indicating a probability of a brain injury of the subject resulting from the fall by the subject for estimating a need of fall specific and subject specific therapy or treatment of the subject.

17. The system of claim 16,
- wherein the instructions further cause the processor to detect the fall by the subject; and
- responsive to detecting the fall by the subject, to determine a time of the fall and to generate the fall data comprising the generated movement data and/or force data for a time period including the time of the fall.

18. The system of claim 16, wherein the instructions further cause the processor to process the fall data to determine a value of a parameter of the fall; and to input the determined value of the parameter of the fall to the prediction algorithm as the fall data.

19. The system of claim 16, wherein the instructions further cause the processor to retrieve each of the fall data, the subject data, and the event data is received from a Personal Emergency Response Systems (PERS) previously configured to monitor the subject.

20. The system of claim 16, wherein the instructions further cause the processor to train the prediction algorithm using a training algorithm configured to receive an array of training inputs and known outputs, wherein a training input comprises at least one of a property, movement, or a force of a subject that experienced a fall, and wherein a known output for a training input comprises a probability of a brain injury.

* * * * *